United States Patent [19]
Knowlton

[11] Patent Number: 5,824,076
[45] Date of Patent: Oct. 20, 1998

[54] SURGICAL METHOD FOR BREAST RECONSTRUCTION USING A NEOVASCULAR TISSUE PEG

[76] Inventor: Edward W. Knowlton, 5478 Blackhawk Dr., Danville, Calif. 94506

[21] Appl. No.: 745,726

[22] Filed: Nov. 12, 1996

Related U.S. Application Data

[63] Continuation-in-part of Ser. No. 408,599, Mar. 22, 1995, Pat. No. 5,765,567.

[51] Int. Cl.⁶ ............................... A61F 2/12; A61B 19/00
[52] U.S. Cl. ................................................ 623/8; 128/898
[58] Field of Search ............................ 623/7, 8; 128/898

[56] References Cited

U.S. PATENT DOCUMENTS

| | | | |
|---|---|---|---|
| 4,264,990 | 5/1981 | Hamas | 623/8 |
| 4,769,036 | 9/1988 | Modir | 623/8 |
| 4,778,465 | 10/1988 | Wilkins | 623/8 |
| 5,092,348 | 3/1992 | Dubrul et al. | 623/8 |
| 5,258,026 | 11/1993 | Johnson et al. | 623/8 |
| 5,301,692 | 4/1994 | Knowlton | 623/8 |
| 5,425,760 | 6/1995 | Rosenberg | 623/8 |

OTHER PUBLICATIONS

Anton et al., "Nipple Reconstruction With Local Flaps: Star and Wrap Flaps," *Perspectives in Plastic Surgery* 5(1):67–78 (1991).
Grossman et al., "An Alternative Technique for Modified Radical Mastectomy With Immediate Reconstruction," *Contemporary Surgery* 36:20–24 (1991).
Maxwell, "Iginio Tansini and the Origin of the Latissimus Dorsi Musculocutaneous Flap," *Plastic and Reconstructive Surgery* 65(5):686–692 (1980).

*Primary Examiner*—Michael J. Milano
*Assistant Examiner*—Tram A. Nguyen
*Attorney, Agent, or Firm*—Lyon & Lyon LLP

[57] ABSTRACT

A surgical method for breast reconstruction, comprising steps of placing a submuscular breast expander beneath a muscle; expanding the breast for a period of time that permits neovascular connections to grow between the muscle and cutaneous tissue which overlays the muscle; and, surgically reconstructing a nipple from the neovascularized cutaneous tissue overlaying the muscle, whereby the expanding step directly contributed an amount of tissue that permitted achievement of the breast reconstruction. The step of recreating the nipple areolar complex can comprise performing a bowtie reconstruction technique.

32 Claims, 2 Drawing Sheets

SURGICAL METHOD FOR BREAST RECONSTRUCTION USING A NEOVASCULAR TISSUE PEG

CROSS-REFERENCE TO RELATED APPLICATIONS

This application is a continue-in-part (CIP) of a parent case (application Ser. No. 08/408,599) filed Mar. 22, 1995, now U.S. Pat. No. 5,765,567.

TECHNICAL FIELD

The invention relates to a medical procedure, and a particular embodiment comprises a surgical method that provides an anatomically correct breast reconstruction from a multi-stage procedure, where an initial stage comprises placement of a breast expander.

BACKGROUND ART

Cancer of the female breast is a significant health matter worldwide. The current treatment of breast cancer often includes surgery, chemotherapy and radiation therapy, and combinations of these three modalities. Approximately one-half of the women in the U.S. that are diagnosed with breast cancer will elect or will require a mastectomy. Thus, mastectomy procedures are commonly used for the treatment of breast cancers.

Mastectomies have been performed since the late 1800s, by a procedure technically known as the Halstead radical mastectomy. During this procedure, the breast tissue and the pectoralis major muscle along with a variable amount of skin including the nipple-areolar complex is removed. Typically, an axillary lymph node dissection is performed concurrently with the mastectomy. This procedure leaves the patient with a Halstead radical mastectomy deformity which is disfiguring and can be emotionally traumatic. The deformity is especially disfiguring when skin grafting is required to close the defect.

The Halstead procedure ("radical mastectomy") has been modified by preserving the pectoralis major muscle (a "modified radical mastectomy"), and by reducing the skin excision to allow for direct linear closure of the defect. As discussed below, mastectomy closure is distinct from post-mastectomy breast reconstruction. Mastectomy closure techniques serve merely to close the excision site, not to reconstruct the shape and aesthetics of a breast.

Post-Mastectomy Closure: In the past, mastectomy closure techniques have included split thickness skin grafts attached directly to the rib cage, in the context of a Halstead radical mastectomy; or simple straight line closure of an elliptical skin excision.

Closure of the skin defect could also involve the immediate incorporation of a cutaneous or myocutaneous tissue flap to at least partially replace the excised tissue. Myocutaneous units are commonly used to cover defects, whether traumatic or post-resectional. Myocutaneous units were prepared as a combination of both skin and muscle, or as a muscle unit that was subsequently skin grafted. Myocutaneous units were transferred as free flaps (flaps detached from intrinsic blood supply), thereafter connecting the unit's axial blood supply to recipient vessels near the defect.

Latissimus dorsi or rectus abdominis myocutaneous flaps were the most frequently utilized myocutaneous flaps for post-mastectomy closure. Some common closure usages for latissimus dorsi flaps included coverage of defects in the head and neck area, especially defects created from major head and neck cancer resection; additional applications included coverage of chest wall defects other than mastectomy deformities. The latissimus dorsi was also used as a reverse flap, based upon its lumbar perforators, to close congenital defects of the spine such as spina bifida or meningomyelocele.

To affect post-mastectomy closure, a latissimus dorsi myocutaneous flap procedure was first combined with the Halstead mastectomy by Dr. Iginio Tansini in Italy in 1906. (Maxwell: *Iginio Tansini and the Origin of the Latissimus Dorsi Musculocutaneous Flap, Plastic and Reconstructive Surgery* (1980) 65(5):686–692) A latissimus dorsi myocutaneous flap having a cutaneous paddle, was used to close the mastectomy defect. This myocutaneous flap had an intrinsic axial blood supply that was critical to the transfer and survivability of the flap.

Prior to the development of the Tansini procedure, random cutaneous flaps had limited survivability due to the paucity of their blood supply. The Tansini procedure did not, however, result in breast reconstruction. The flap was used only to close the chest wall defect.

Post-Mastectomy Breast Reconstruction: Due to the adverse characteristics of a mastectomy deformity, either following a radical mastectomy or a modified radical mastectomy, many women opt for post-mastectomy breast reconstruction. Reconstruction can take place contemporaneously with the mastectomy, or at a later time in single or multiple stages.

To achieve breast reconstruction, it is common to use a submuscular breast expander and/or a permanent implant in conjunction with some form of a mastectomy closure technique. A breast expander allows for, and generally requires, sequential addition of fluid to stretch the remaining breast tissue. Accordingly, expanders or implants are inserted beneath the mastectomy incision, and have been used as a method for either immediate or delayed breast reconstruction.

Post-Mastectomy Use of Myocutaneous Flaps: There are several disadvantages to post-mastectomy use of former myocutaneous flaps, in the contexts of excision closure and post-surgical breast reconstruction. In either of these contexts, most procedures cause a significant transverse scar across the chest. The donor site scar on the back is also substantial. When such procedures are used and a breast is reconstructed, the disadvantages are exacerbated since there is a large elliptical paddle of skin across the breast. This skin paddle has different pigmentation than the adjacent breast skin. Furthermore, the large flap of skin does not adequately recreate the contour of the breast.

Circumareolar Mastectomy: Previously, major resections of skin occurred during radical or modified radical mastectomy procedures. More recently, skin resection has been limited to the nipple-areolar complex, through a circumareolar or periareolar incision. Modified radical mastectomies with circumareolar incisions have been performed on patients who did not have pre-existing invasion of the surrounding breast skin. When the skin excision is limited to the region of the nipple-areolar complex, the skin envelope of the breast is preserved.

When a circumareolar mastectomy was performed via an excision of the nipple-areolar complex, a straight line closure with insertion of breast expander has been used. (Grossman et al.: *An Alternative Technique for Modified Radical Mastectomy with Immediate Reconstruction. Contemp. Surg.* (1991) 38(6):20–24). With this post-mastectomy reconstruction, the incision was closed with a straight line closure, accordingly the reconstructed breast was skin deficient compared to the contralateral breast. This tissue shortage frequently required a repositioning surgery of the contralateral breast, resulting in scarring on both the contralateral and ipsilateral breasts. Moreover, the reconstructed breast lacked any nipple-areolar complex.

Myocutaneous Flap Reconstructions Following Circumareolar Mastectomy: Trans-rectus abdominis muscle flaps (TRAM flaps) have also been used in combination with a circumareolar mastectomy. TRAM flaps have served to close a mastectomy defect and to provide breast reconstruction. With the TRAM flap, a circular skin island was designed and transferred to the mastectomy defect. In some instances, a nipple-areolar reconstruction was performed. However, this skin island did not result in a reconstructed breast having a nipple-areolar complex with the same projection as a normal breast. In a TRAM flap procedure, the subcutaneous tissue of the flap, rather than a breast implant, fills the void left by the removal of the breast tissue. As with other myocutaneous flaps, projection of the reconstructed nipple-areolar complex was poor. The transferred rectus abdominis muscle functions principly as a conduit of the vascular supply. Thus, the majority of the reconstructed breast volume was filled by adipose subcutaneous tissue of the TRAM myocutaneous unit.

A physician and patient must weigh a number of issues when contemplating use of a TRAM flap. The flap failure rate is higher with TRAM flaps as compared to latissimus dorsi flaps, because the circulation of the myocutaneous unit is less reliable. Since subcutaneous adipose tissue provides the majority of the reconstructed breast volume with former TRAM flaps, fat necrosis of this tissue was a significant complication with this procedure. If fat necrosis of the adipose tissue occurs, calcifications and connective tissue masses can result. These sequelae can exacerbate the difficulty of diagnosing a chest wall cancer recurrence, and diminish the quality of the reconstructed breast.

The donor site scar can be an issue with the TRAM procedure: the scar is located on the lower abdomen and runs hip to hip. Patients may be subject to abdominal wall weakness and hernia formation after one or two rectus muscles are transferred to the breast. Since there is a single donor site on each patient, the TRAM flap procedure can be performed only once. Breast reconstruction for any subsequent breast cancer would require the use of a different technique. Use of a TRAM flap is limited if the woman has any abdominal scars or if the woman has an inadequate amount of subcutaneous tissue. These limitations with a TRAM flap were especially problematic when attempting to reconstruct a large breast. However, some women prefer a TRAM procedure; it can often achieve breast reconstruction without use of an implant, and it can serve as abdominoplasty if a woman has excess abdominal tissue.

Former free gluteal flaps have also been designed which function in a similar fashion to the former TRAM flap. The former gluteal flap has the same disadvantages as the former TRAM flap, as well as the disadvantages typically attendant to free flaps.

Limitations with Former Reconstructions: In general, there are several significant drawbacks with prior breast reconstruction procedures when used after a standard modified radical mastectomy. Severe scarring is one of the most serious problems. Due to the substantial contour distortion produced by these techniques, a reliable method of aesthetically pleasing total breast reconstruction could not be performed. Moreover, repositioning of the contralateral breast was often required, consequent to the limited amount of tissue available for reconstruction on the mastectomy side. After a breast was reconstructed, the breast had a distinctly artificial appearance due to the large amounts of skin resection and scarring.

DISCLOSURE OF THE INVENTION

Disclosed herein is a method for breast reconstruction comprising: reconstructing a nipple and or areola from neovascularized myocutaneous tissue of the breast. The muscular component of the myocutaneous tissue can comprise pectoralis major muscle, serratus anterior, rectus abdominous or latissimus dorsi muscle. The method can comprise a step of placing a breast expander beneath the muscle which provides a muscular component to the myocutaneous tissue.

Also disclosed herein is an embodiment of a surgical method for breast reconstruction, comprising steps of: placing a submuscular breast expander beneath a muscle; expanding the breast for a period of time that permits neovascular connections to grow between the muscle and cutaneous tissue which overlays the muscle; and, surgically reconstructing a nipple-areolar complex from the neovascularized cutaneous tissue overlaying the muscle. The method can be performed following a mastectomy or post-traumatically. If a post-mastectomy procedure is performed, the step of placing the expander can occur through the mastectomy incision, following which the mastectomy incision is closed. The expander used in the method can be an expander comprising a means for segmental expansion. Typically, the expander is placed beneath a pectoralis major muscle. Preferably, the step of recreating the nipple areolar complex comprises use of a bowtie reconstruction technique from the neovascularized tissue.

MODES FOR CARRYING OUT THE INVENTION

As disclosed herein, neovascularized tissue is used for breast reconstruction, whereby a nipple-areolar reconstruction is performed that results in enhanced nipple-areolar projection and a very natural aesthetic outcome. The neovascularized tissue can be a cutaneous peg or island which comprises cutaneous tissue, subcutaneous tissue and inherent circulatory vessels; or, a myocutaneous peg which comprises muscular tissue, cutaneous tissue, subcutaneous tissue and inherent circulatory vessels. As used herein, cutaneous is defined to mean a fully epithelialized or a partially deepithelialized flap.

As used herein a flap can be a free flap or a flap where the inherent vessels remain connected (e.g., a pedicled flap). If connected to the native vascular supply, the flap can be moved to a different location on the body, or can be utilized at its native location. As defined herein, reconstruction comprises a procedure to provide any change in the shape, volume or contour of a breast. Thus, a reconstruction can be a post-mastectomy procedure, a post-traumatic procedure, or a procedure done to enlarge or decrease the volume of the breast. A preferred reconstruction occurs as a separate stage following a mastectomy; it can take place over one or more post-mastectomy surgical procedures.

In accordance with embodiments of the invention, a multistage procedure comprises: 1) a mastectomy is performed with contemporaneous placement of an expander, and a subsequent procedure when a tissue flap reconstruction is performed; 2) a mastectomy, a subsequent procedure when an expander is placed, and a subsequent procedure when a tissue flap reconstruction is performed; 3) revisions to a previous reconstruction; or, 4) the placing or modifying of breast implant materials.

Breast Reconstruction Comprising a Neovascular Cutaneous or Myocutaneous Peg Discussed herein is information that allows a surgeon to recreate symmetrical breasts following a mastectomy or trauma. The method reduces the magnitude of surgery heretofore required for breast reconstruction and produces improved aesthetic results.

Symmetrical breast reconstruction requires an appreciation of the contours of each individual aesthetic unit of the breast. The nipple, the areola, and the projection of the entire nipple-areolar complex in relation to the overall contour of the breast mound must be taken into account to achieve an ideal breast reconstruction. Furthermore, creation of a lasting symmetrical breast reconstruction requires an assessment of changes that occur over time with both breasts. As discussed herein, reconstruction with components that are similar in both breasts provides an improved long-term result.

For example, completely autologous methods have been advantageously employed with unilateral reconstruction. See for example U.S. Pat. No. 5,301,692, issued 12 Apr. 1994 to the inventor herein, Dr. Edward Knowlton; this patent is fully incorporated by reference herein. The autologous peg flap offers the patient an excellent method of immediate and total breast reconstruction whether the TRAM or latissimus dorsi flap is used. Further aspects of the autologous peg flap are described in copending U.S. application Ser. No. 08/408/599, which is fully incorporated by reference herein.

An autologous peg flap, such as from the TRAM or latissimus dorsi muscle, avoids double tier scarring and pigmentary discrepancy of a standard flap reconstruction. Additionally, in fully autologous methods or the present implant reconstruction methods, contour restoration is facilitated by the circular recoil of the breast envelope around the reconstructed nipple-areolar complex.

Accordingly, it is now possible to accurately recreate any breast contour without the pigmentary discrepancy and double tier scar of a standard flap reconstruction. However, even fully autologous reconstruction methods have limitations, as such they can be contraindicated or disadvantageous in certain clinical scenarios.

For bilateral breast reconstruction, it is presently preferred that expander implant methods be used; this is due to concerns of significant donor site morbidity which is a concern because of the two donor sites with bilateral autologous breast reconstructions. As disclosed herein, unilateral implant reconstruction with a pectoralis peg technique preferably comprising both a bowtie technique, and use of U.S. regulatory agency approved implant, is an excellent alternative for unilateral autologous reconstruction.

When a skin preservation mastectomy has been performed, the present method of breast reconstruction permits that the subsequent surgical incision is camouflaged within the perimeter of the reconstructed nipple areolar complex. Thus, the present method, comprising neovascularized tissue and an implant following a skin preservation mastectomy, eliminates visible scarring on the reconstructed breast. Moreover, neither autologous flaps nor skin grafts are required.

Pectoralis Peg Procedure with Implant:

Disclosed for the first time herein is the use of the unique vascular features of a healed mastectomy site. These vascular features comprise adherence of the breast skin envelope to the underlying pectoralis muscle, with the concomitant growth of neovascular perforators from the muscle into the skin.

Concerns of breast envelope necrosis have limited the use of immediate reconstructions. However, a staged technique, such as disclosed herein, allows neovascularization of the mastectomy site, and provides additional safety and reliability to the overall reconstruction procedure. This is especially relevant for larger breasts where impaired circulation and necrosis are of particular concern.

With the present staged techniques, a surgeon can create an island pectoralis peg that has sufficient circulation for the creation of a nipple areolar complex. Thus, a circular myocutaneous island, with a robust neovascular blood supply, is used as a myocutaneous source for a peg to be used in nipple-areolar reconstruction. In preferred embodiments, reconstructed nipple-areolar complex does not require an areolar skin graft.

Without resorting to distant tissue sources (such as is required with autologous flaps), the pectoralis peg technique accurately recreates the specific contours of the breast. As compared to autologous flap methods involving free or pedicled flaps, the pectoralis peg procedure is based upon a local neovascularized myocutaneous territory, and is an excellent alternative for a patient who is concerned about the potential morbidity that accompanies the preparation and transfer of an autologous flap. The present procedure comprising a neovascularized myocutaneous peg is also an excellent choice for those patients for whom a more involved single-stage surgery is not desired or is contraindicated.

Thus, in a preferred embodiment, the myocutaneous pectoralis peg is combined with a breast implant. This new procedure offers several advantages. Most significantly, the overall scarring and magnitude of the reconstructive process is reduced. The pectoralis peg procedure can be used with either a skin resection or a skin preservation mastectomy. In either context, neovascularized tissue over a muscle is employed in the recreation of the nipple-areolar complex. It is preferred that the pectoralis peg be employed with a skin preservation mastectomy. Moreover, the pectoralis peg technique can also be used to revise a suboptimal or inadequate breast reconstruction.

A post-mastectomy pectoralis peg reconstruction preferably occurs as follows: Following a skin preservation mastectomy, time for sufficient healing is provided so that there is neovascular adherence of the remaining breast skin envelope to the underlying pectoralis major. Neovascularization of the skin envelope from the pectoralis muscle, with its axial blood supply, results in an augmented blood supply to the cutaneous tissue. The growth of neovascular musculocutaneous perforators is perpendicular to the skin surface. As a result, the presence of any mastectomy incisions on the skin surface do not generally adversely affect the circulation of the cutaneous pectoralis peg.

In an alternative embodiment, the pectoralis peg procedure is combined with an autologous flap procedure. The autologous flap provides breast volume, and avoids the use of a permanent implant. The autologous flap can be harvested and transferred in an open or endoscopic surgical procedure. For example, when a latissimus dorsi flap is used, the latissimus dorsi muscle provides neovascular connections to the overlaying breast skin; if a pectoralis muscle is also a muscle underlaying the breast skin, it also functions to provide neovascular connections to the skin. Other muscles which provide neovascular connections include the serratus anterior or the rectus abdominous muscles.

Thus, post-surgical neovascularization effectively creates well vascularized myocutaneous tissue. The resulting level of vascularization is greater than that of a random cutaneous flap/island. As disclosed herein, it has now been found that the neovascularized myocutaneous breast tissues is an ideal platform for nipple-areolar reconstruction. The bowtie technique of nipple-areolar reconstruction is presently preferred.

Nipple-Areolar Reconstruction:

There are several approaches to nipple-areolar reconstruction. In certain embodiments, a quadruped tissue shape has been used to create a nipple, with graft tissue used to create an areola.

A preferred nipple reconstruction is the "bowtie" technique of Knowlton. The Knowlton "bow tie", procedure is a development beyond principles used in "star" nipple reconstruction. (Anton, M.A., et al., Perspect. Plast. Surg. (1991) 5:67) In the Knowlton procedure, the vertical limbs of the "bowtie" are designed as rectangles and extend to the perimeter of the "peg". (FIG. 1) In an embodiment of the Knowlton "bowtie" procedure, the vertical limbs/tabs of the bowtie are designed as "fan shaped" rectangles which are larger distally and narrower more proximally (proximal and distal defined relative to the connection of a rectangular tab to the nipple tab).

Figure 1:
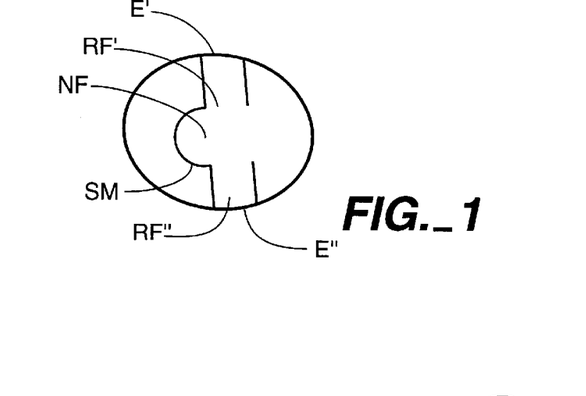
FIG. 1 depicts the incision lines of a bowtie nipple areolar reconstruction.
Figure 2:
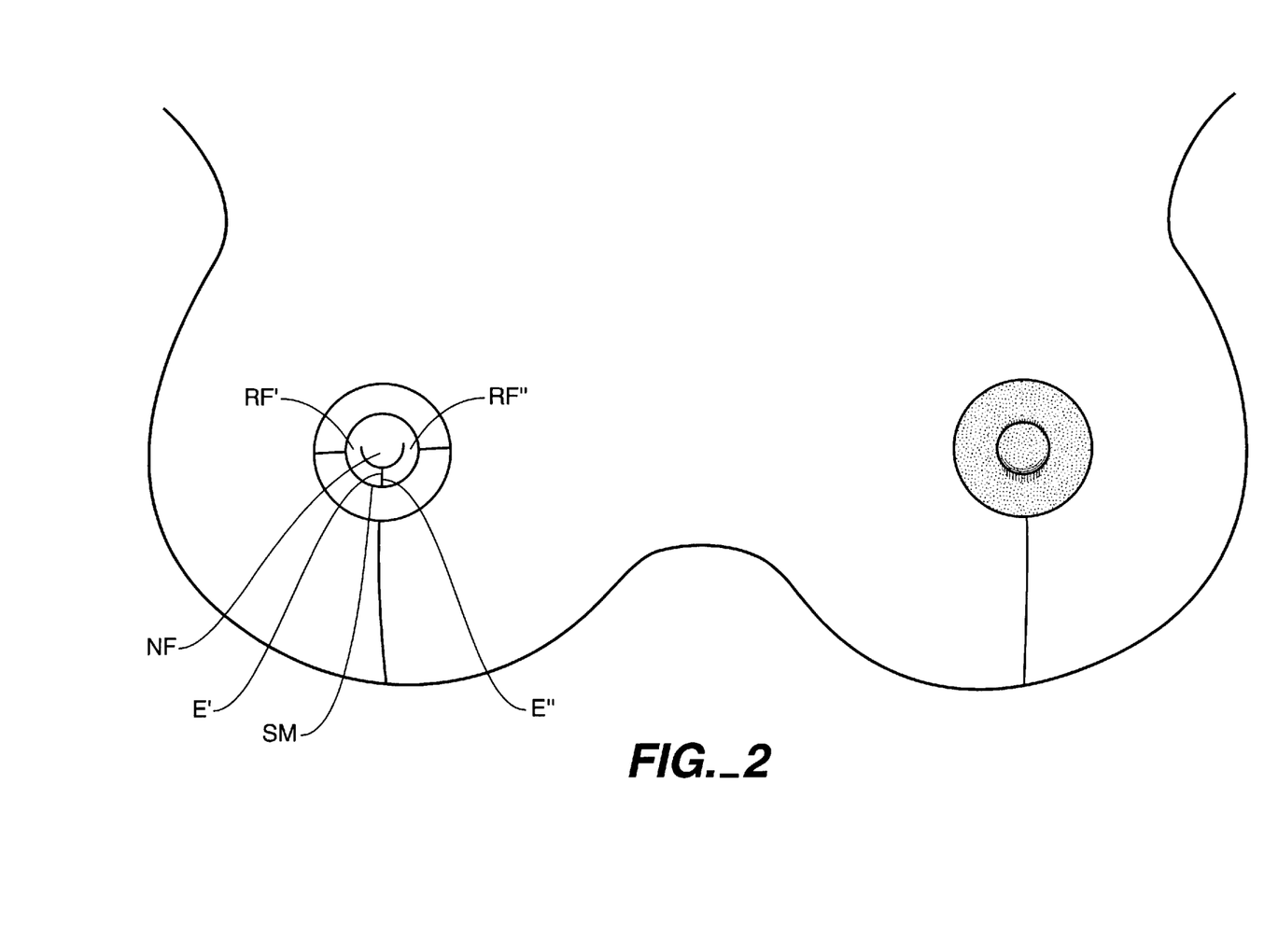
FIG. 2 depicts a bowtie reconstruction with the elements sutured together on the breast.

Thus, to create a bow tie reconstruction, the two rectangular flaps (RF' and RF") and a rounded nipple flap (NF) are dissected. (FIG. 1) The flaps are preferably dissected so as to include a variable amount of subcutaneous tissue muscle and/or scar tissue, to provide volume to the reconstructed nipple. Referring to FIGS. 1 and 2, closure of the nipple flap donor site occurs by suturing of the rectangular flaps to the margin of semicircular incision, and advances the donor semi-circular incision (semicircular margin SM).

In an embodiment with creation of laterally wider rectangular flaps (i.e., fan shaped), closure of the divergent, laterally wider donor sites produces a result that further enhances the conical shape of the reconstructed areola. As depicted in FIG. 2, the distal ends (E' and E") of the rectangular nipple flaps are sutured together resulting in placing of a margin (the inferior margin) of each rectangular flap in close approximation to the inner margin of the underlying semi-circular margin SM (the nipple flap donor site), and resulting in placing of a margin (the superior margin) of each rectangular flap beneath the nipple flap NF. The margin of nipple flap NF is sutured to the superior margins of the rectangular flaps and the semicircular margin is sutured to the inferior margins of the rectangular flaps to create a projecting nipple.

The perimeter of the reconstructed nipple-areolar complex is then circumscribed with an appropriately sized circular template to facilitate obtaining a substantially circular shape for the reconstructed complex. Using the circular template, the skin outside of the "peg" flap is de-epithelialized to create a reconstruction with a perimeter that corresponds to the shape of an areolar perimeter. A variation is to use the harvested areola as a full thickness skin graft over a de-epithelialized areolar portion of the "peg". If there is reduced circulation, to the region of the reconstructed nipple, the perimeter of the peg/island is not circumscribed. Instead, an area corresponding to the areola is deepithelialized and graft tissue is provided to recreate the areola; alternatively, an areola is recreated by tattooing. If the contralateral breast is intact, the area of the areola recreated by skin grafting or tattooing is designed to correspond to the contralateral areola.

With a bowtie technique, the height of the nipple is determined by the width of the bowtie flaps and the contour of the areola is determined by the width of the defect in which the reconstruction occurs. Modifications to the shape of the nipple flaps and modifications of the donor defect have achieved specific three-dimensional contours with bowtie reconstruction. For example, rectangular shaped flaps and donor defects will produce a flatter contour when the donor defect site is closed.

Fan shaped tabs of the "bowtie" which are wider at their periphery, have produced a more conical projection to the reconstructed nipple-areolar complex. In another embodiment of the bowtie technique, concave tabs are prepared. Concave bowtie flaps are wider proximally and distally than they are at an intervening location. Accordingly, the donor site is defined by margins which have a convex shape; use of this embodiment has created a more convex, i.e., rounded areolar contour.

In a presently less preferred embodiment, a nipple can be reconstructed from a superiorly pedicled quadruped flap, as known in the art. Alternative methods of nipple-areolar reconstruction are known to those skilled in the art. Such methods include nipple mound reconstruction with quadruped, triped or biped pedicled flaps; or with subcutaneously pedicled quadruped or triped flaps. Nipple projection can also be obtained through the use of ear cartilage, or the use of a subcutaneously implanted nipple prosthesis.

If the nipple is raised from the area of the cutaneous peg without additional skin grafting, subsequent tattooing will occur over the entire nipple-areolar complex, rather than just to the nipple area.

The bowtie technique is commonly used without an areolar graft; and has most frequently been used with autologous myocutaneous peg flaps such as the latissimus dorsi or trans-rectus abdominis muscle (TRAM). These flap-based reconstructions are more extensive and debilitating than present invention; the flap-based procedures involve the transfer of autologous tissue from a separate donor site to the mastectomy defect. Nevertheless, the bowtie technique can be used for either fully autologous or for the present expander-based reconstructions comprising a neovascularized myocutaneous peg. Accordingly, use of the bowtie technique to control the contour of the nipple-areolar complex has been well demonstrated.

Pectoralis Myocutaneous Peg With Bowtie Nipple Reconstruction

In accordance with an embodiment of present invention, without a requirement to resort to use of distant tissue sources, the bowtie method in conjunction with the pectoralis peg technique greatly reduces surgical scarring and produces excellent three-dimensional breast contour. This occurs by use of tissues of the expanded breast envelope for this reconstruction. A further advantage of the present invention is that modification of the bowtie flaps with direct closure of the donor defect has produced contour results that very closely recreate the specific geometry of the contralateral nipple-areolar complex.

The foregoing aspects of the invention allow the surgeon greater latitude when designing the bowtie flaps for the nipple-areolar reconstruction.

With the pectoralis peg procedure, preparation and harvesting, and transfer of autologous myocutaneous flaps and/or skin grafts are avoided. Moreover, separate incisions on the breast are not required.

In contrast to single stage completely autologous reconstruction methods without an implant, the pectoralis peg procedure with bowtie nipple-areolar reconstruction typically requires two less involved stages. For this reason, the pectoralis peg procedure is medically indicated for certain patients. Because each stage is less involved, they are generally less debilitating to the patient. It can also be advantageous that the two stages of the pectoralis peg procedure are separate, so that the patient can regain strength and rehabilitate.

Thus, a preferred embodiment of the invention is a pectoralis peg procedure performed as a two-stage technique. The initial stage involves the insertion of a submuscular (i.e., subpectoral) breast expander. The second stage involves the insertion of a permanent implant and creation of the nipple-areolar complex.

In the medical-surgical context, there are specific roles for both autologous and implant reconstructions.

Procedures employing a pedicled autologous flap offer patients an excellent method of immediate and total breast reconstruction, whether a TRAM of latissimus dorsi flap is used. Upon use of an autologous flap, the recreation of the nipple areolar complex can be performed at the time of reconstruction or at a later time. With the pectoralis peg method with the preferred bowtie reconstruction, delayed reconstruction of the nipple areolar complex is possible without areolar skin grafts or flap donor incisions.

EXAMPLES

The most common context in which the pectoralis peg reconstruction occurs is following a mastectomy. It is understood that the present invention can also be performed post-traumatically. The more common scenario of reconstruction following a skin resection or skin preservation mastectomy will be discussed.

Initial Stage: In the first stage of a pectoralis myocutaneous peg reconstruction procedure, a subpectoral breast expander was inserted. The initial stage of reconstruction (breast expansion), differs depending on the type of mastectomy that had been performed. For a skin resection mastectomy, appreciable expansion of the breast envelope is generally required. In contrast, a skin preservation mastectomy requires less expansion, and produces less scarring of the breast envelope.

To complete the initial stage of reconstruction, the circular nipple-areolar defect was closed with a double or multiple V-Y advancement to limit lateral extension of the scar; this step serves to confine the scar within the eventual site of the reconstructed nipple-areolar complex.

A double or multiple V-Y closure of the circular mastectomy incision (the site of the former nipple-areolar complex) creates a bowtie-shaped redundancy. The bowtie shaped redundancy that results from the double or multiple V-Y closure is readily expanded in a segmental fashion. The elongated bowtie-shaped redundancy is enveloped inward during the "bowtie" technique nipple areolar reconstruction. (Coincidentally, the term bowtie is used in two different contexts in this embodiment: the shape of the sutured mastectomy incision, and as the technique for nipple-areolar reconstruction.)

The preexisting scars of the V-Y closure do not compromise the design of the bowtie flaps. Nipple-areolar reconstruction during the second stage is not impaired due to the presence of neovascular musculocutaneous perforators that are oriented perpendicular to the skin surface. Sufficient time is provided following the first stage so that neovascularization of the breast skin occurs. This generally occurs between 12 and 24 weeks post-surgery.

Subsequent Stage: The second stage of the reconstruction involved the creation of a nipple-areolar complex along with insertion of a permanent implant. Preferably, insertion of the permanent implant and creation of the nipple-areolar complex each comprise use of the bowtie incision. An advantageous aspect of the present invention is that creation of the bowtie can obscure the initial mastectomy incision within the reconstructed nipple-areolar complex.

Typically, the bowtie flaps are raised full thickness including the pectoralis major and the scar capsule around the expander. The flaps/tabs of the bowtie were located within the neovascularized "peg". If any of the "tabs" of the bowtie are crossed by a mastectomy scar, additional pectoralis muscle is harvested in order to preserve the circulation of those tabs. It is to be noted that harvesting of excessive muscle can, however, compromise circulation to the reconstructed areola.

The bowtie incision was subsequently used as an access incision for removal of the subpectoral expander and for placement of an (optional) permanent implant. Adequate exposure through the bowtie incision was also provided so that the surgeon can carry out scar capsule modification of the inframammory fold if indicated. Direct closure of this full thickness donor site defect created the desired contour of the nipple areolar complex.

An implant may not be required for small breasted women. For example, the scar capsule that surrounded the expander may become fluid filled, thereby providing sufficient volume for a small breasted woman. Alternatively, a permanent implant is not required where the reconstruction comprises tissue grafting or culture to provide volume. For example, the tissue culture can comprise breast, muscle, mucosa, synovium or adipose tissue; a preferred graft embodiment can comprise adipose tissue. When performing tissue grafting or culture to provide breast volume, it is preferred to use a textured breast expander to facilitate blood flow to the reconstructed breast.

Following the creation of the nipple, e.g., by the preferred bowtie method, the perimeter of the reconstructed nipple-areolar complex is circumscribed with a circular template. Any irregular "dog ear" skin redundancy of adjacent breast skin is released by modest undermining of the adjacent breast skin in the subdermal plane; this redistributes the redundancy evenly, and generally does not disrupt the neovascular circulation of the reconstructed nipple-areolar complex. A purse string suture is inserted to close the circular skin defect created by circumscribing the template. Suturing the defect also serves to project the reconstructed nipple areolar complex to an elevated position.

Thus, improved contour results, including projection of the entire nipple-areolar complex, are achieved due to the bowtie technique and by purse string closure of the breast skin around the areolar perimeter.

Post operative nipple atrophy of approximately 30% should be considered when planning and performing the procedure. However, an exception to this degree of atrophy is when the bowtie technique is used with the peg latissimus dorsi flap. For the latissimus dorsi embodiment, little or no atrophy is encountered, and any dog ear type redundancy of the bowtie is corrected by skin resection of flap skin that surrounds the peg.

A preferred pectoralis peg reconstruction following a skin preservation mastectomy, provided that the scarring for both the oncologic and reconstructive surgeries was reduced to a single incision that is well camouflaged within the reconstructed nipple-areolar complex. Donor site scars for any autologous flap, or for any areolar skin graft are also avoided in most cases.

Accordingly, a reconstruction comprising a pectoralis myocutaneous peg technique in conjunction with a bowtie nipple-areolar reconstruction technique is highly advantageous. The pectoralis peg reconstruction utilizes a neovascularized myocutaneous peg/island of the pectoralis major muscle; this reconstruction is an excellent alternative for the patient who is concerned about the scarring and potential donor site morbidity of an autologous flap reconstruction.

Without the need to harvest and use distant tissue sources, the pectoralis peg technique has accurately and reliably recreated the specific contours of the breast. By use of the present invention, superior aesthetic results were achieved compared to previous implant techniques. Furthermore, revisions to a suboptimal reconstruction, performed either with or without subpectoral implants, can be performed in accordance with the invention.

Segmental Expander for Breast Tissue:

A segmental expansion of the breast envelope in the area of the pectoralis peg allows for recreation of the nipple areolar complex without distortion of the overall breast contour. Commonly used expanders are designed to expand all or large areas of the breast envelope.

Certain expanders which expand less than the entire breast envelope exist. These non-total expanders expand a full region of the breast, e.g., the inferior pole, to a greater extent than other regions. For example, the McGHAN ANATOMICAL and the MENTOR CONTOUR PROFILE expanders are fabricated to expand the inferior pole of the breast. However, neither of these models provide the means to selectively expand a circular (i.e. tubular/conical) segment of the breast envelope. The creation of a tubular shaped segment best provides additional breast skin envelope to be utilized for the bowtie nipple-areolar reconstruction. As noted herein, the bowtie technique recreates the nipple-areolar complex within the pectoralis peg flap, and does not require any additional flap or graft incisions.

A segmental breast expander is disclosed herein. The segmental breast expander design of the invention can comprise a configuration with additional expander material, so that when expanded the segment comprising the additional material produces expansion of a tubular/conical segment. Alternatively, the segmental expander can comprise a portion of differential (i.e., greater) elasticity than the remainder of the expander; when expanded, the region if greater elasticity protrudes and produces expansion of a tubular/conical segment. Alternatively, the expander can comprise both a segment of additional material and a region of relatively increased elasticity. The later embodiment is presently preferred as it most readily provides the ability to increase the expanded segment during the period of expansion.

Segmental breast envelope expansion, in conjunction with a pectoralis peg technique and a bowtie reconstruction results in a conical shaping of the tubular segment upon creation of the nipple areolar complex. Moreover, contour distortion of the adjacent breast envelope is minimized.

This segmental expansion process is conversely analogous to the treatment of a tubular breast deformity where a circumareolar segment of skin is resected to restore a normal contour. With segmental expansion in a mastectomy deformity, the excess skin is created and then used to recreate the nipple areolar complex. The creation of an elongated segment is aided with a skin preservation mastectomy.

Figure 3:
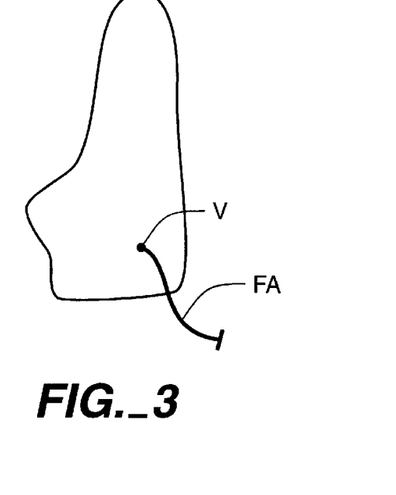
FIG. 3 illustrates an expander embodiment which comprises a contoured expander surface.
Figure 4A:
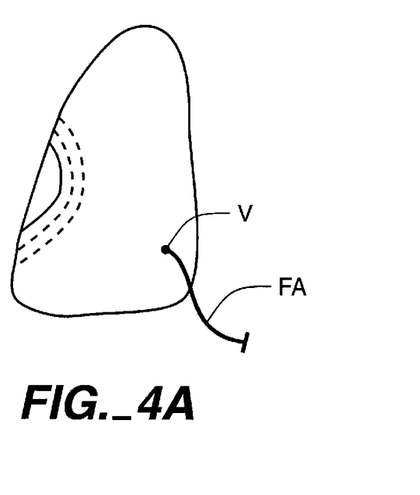
FIG. 4A–C illustrates an alternative embodiment of an expander for use with the method of the invention, this expander embodiment comprises an elastic "telescoping" section which is depicted as progressively expanded in the FIG. 4A through 4C.
Figure 4B:
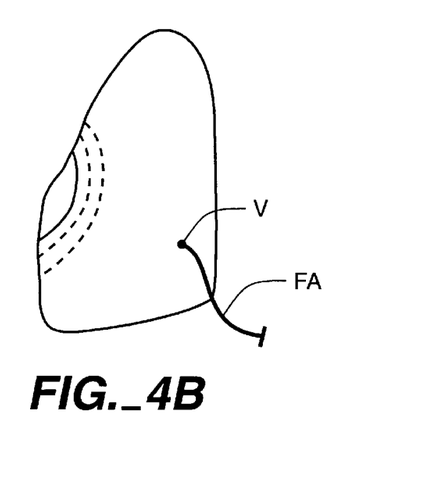
Figure 4C:
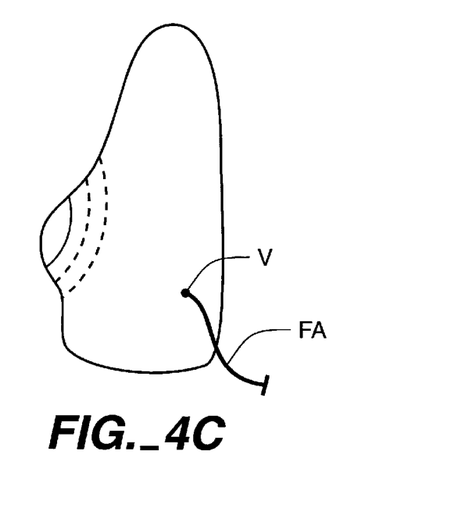

Accordingly, an embodiment of the selective segmental expander can comprise fabrication of the expander so that it has a contour as shown in FIG. 3. In FIGS. 3 and 4, "VI" represents a valve and "FA" represents a filling apparatus for the expander. Another embodiment of a segmental expander is provided by altering the elasticity of the expander envelope without contour fabrication; this embodiment is depicted in FIG. 4 A–C. The elastic portion of the expander is enlarged, e.g., by provision of fluid to an expander compartment as indicated sequentially in FIG. 4 A–C. A combination of both surface fabricated and elastic surface embodiments can be employed.

Alternative embodiments of the expander comprise features that relate to fixation and alignment within the submuscular pocket. In one embodiment, fixation tabs in the telescoping (e.g., the elastic portion) segment will secure and orient the expander in the submuscular pocket. Optionally, enhanced fixation can be obtained by increasing the texturing of the telescoping segment under the pectoralis peg; such texturing will also promote neovascularization. One can select a pattern of texturing which is known to enhance or facilitate neovascularization. In addition, texturing of the telescoping expander segment will incite a more hyperemic scar capsule. Infrared and echo Doppler flow studies show augmented neovascular circulation to this area upon use of textured expanders.

In alternative embodiments, a valve is incorporated within the telescoping segment and has a magnetized metal backing similar to that in the McGHAN ANATOMICAL expander. This magnetized backing is typically used as a valve finder. Moreover, the magnetized backing can also interact with an external magnet of opposite polarity, to physically reinsert a dislodged telescoping valve into the expanded segment of the breast envelope.

Another embodiment of the expander is a combination expander/permanent implant. The combination embodiment comprises a remote valve that can be subsequently removed; upon removal of this valve, the implant is self sealing. This type of valve is found, for example, in the SILTEX SPECTRUM (Mentor H-S, Inc. Santa Barbara, Calif.).

A combination expander/permanent implant does not require replacement during the second stage of the pectoralis peg reconstruction. During the peg procedure with the combination embodiment, the expander implant is partially deflated. The implant can be subsequently reinflated to allow for additional volume adjustment and to smooth the purse string pleating around the reconstructed nipple areolar complex. Subsequent removal of the remote valve is easily achieved under local anesthesia.

In still another embodiment, a drug delivery chamber is placed within the incorporated valve. This overlying drug delivery chamber preferably comprises a porous membrane that allows diffusion at a predetermined rate into the tissue. For example, a preferred drug for inclusion into the drug delivery chamber is PROCURAN, a growth hormone derivative which promotes angiogenesis. Diffusion of an angiogenesis agent into the area of the pectoralis peg provides for additional circulation, and facilitates creation of the nipple areolar complex.

Further embodiments entail the incorporation of an energy delivery systems such as an R.F. electrode array that will induce scar collagen formation in the scar capsule around the expander. R.F. modulation of intracellular metabolism could also induce the multiplication and hypertrophy of preferred cell types, such as myocytes or adipocytes, to provide an autologous filler without the surgical transfer of a flap and/or placement of a permanent implant.

Still another embodiment comprises the injection into the scar capsule cavity of a viscus body fluid after the removal of the expander. The injected body fluid comprises a viscous colloid mixture that prevents contraction and does not diffuse easily across the scar capsule. For example, the ground substance hyaluronic acid acts as a lubricant and a filler with a relatively high molecular weight and viscosity. This material is now genetically produced by Genzyme Corporation (Boston, Mass.). Combined with a colloid to prevent diffusion, this substance functions as a nonprosthetic volume replacement for breast reconstruction.

With the development of tissue culture techniques that provide sheets of autologous epithelial cells, creation of a epithelial cell-lined breast cavity is possible. For example, the epithelial tissue can be mucosal or synovial tissue. For example, prior to the first stage insertion of an expander, a sample of the patient's mucosal or synovial tissue is obtained; this tissue is cultured and grown into a sheet that is wrapped around the expander during the first stage of the reconstruction. Following expansion of the breast envelope, the expander is removed. The breast cavity lined with synovial or mucosal cells is filled with a protein colloidal mixture such as mucin and hyaluronic acid.

Still another approach is to inject synovial cell-protein colloid mixture into the breast cavity to obtain a honeycomb lattice of joint fluid and synovium; alternatively, a mucosal cell-protein colloid mixture is injected. The growth hormone derivative PROCURAN can be included with the mixture culture to promote angiogenesis. Essentially, an autologous implant without prosthetic material is created. As appreciated by one of ordinary skill in the art, periodic injection or aspiration into the breast pocket will be necessary until homeostasis is created in the biological system.

Closing:

Although the present invention has been particularly described with regard to open surgical techniques, other surgical techniques are within the scope of the invention. For example, endoscopic dissection of a cutaneous or myocutaneous peg and the mastectomy site can be performed. Although certain embodiments of the procedure have been set forth, these embodiments are not to be construed as limiting the invention. Other medical techniques and sequences of performing the steps of the procedure can be utilized, as will be known to those of skill in the art. The procedure of the present invention is disclosed herein.

It must be noted that as used herein and in the appended claims, the singular forms "a", "and", and "the" include plural referents unless the context clearly dictates otherwise. Thus, for example, reference to "a formulation" includes mixtures of different formulations and reference to "the method of treatment" includes reference to equivalent steps and methods known to those skilled in the art, and so forth.

Unless defined otherwise, all technical and scientific terms used herein have the same meaning as commonly understood by one of ordinary skill in the art to which this invention belongs. Although any methods and materials similar to equivalent to those described herein can be used in the practice or testing of the invention, the preferred methods and materials are now described. All publications mentioned herein are incorporated by reference herein, to describe and disclose specific information for which the publication was mentioned.

What is claimed is:

1. A surgical method for breast reconstruction, comprising steps of:
   placing a submuscular breast expander beneath a muscle;
   expanding the breast for a period of time that permits neovascular connections to grow between the muscle and cutaneous tissue which overlays the muscle; and,
   surgically reconstructing a nipple from the neovascularized cutaneous tissue overlaying the muscle, whereby the expanding step directly contributed an amount of tissue that permitted achievement of the breast reconstruction.

2. The method of claim 1 further comprising:
   providing mastectomy on a breast through an incision, prior to the expander placement step.

3. The method of claim 2 wherein the step of placing the expander further comprises placing the expander through the mastectomy incision; and,
   closing the mastectomy incision on the breast.

4. The method of claim 3 wherein the mastectomy incision closing step comprises use of double or multiple V-Y advancement.

5. The method of claim 1 wherein the expander placing step comprises placing an expander comprising a means for segmental expansion; and, whereby the nipple reconstruction step comprises reconstruction from tissue expanded by the means for segmental expansion.

6. The method of claim 1 the expander placing step comprises placing an expander beneath a pectoralis, serratus anterior, latissimus dorsi or rectus abdominous muscle.

7. The method of claim 1 wherein the step of recreating the nipple further comprises recreating a nipple areolar complex.

8. The method of claim 7 wherein the step of recreating the nipple areolar complex comprises performing a bowtie reconstruction technique.

9. The method of claim 8 further comprising steps of:
   dissecting a nipple flap and two rectangular flaps on the neovascularized cutaneous tissue, the two rectangular flaps connected at their respective proximal margins to the nipple flap, the rectangular flaps connected on opposite sides of the nipple flap; and,
   suturing the nipple flap to the two rectangular flaps and suturing closed a donor defect for the nipple flap and the two rectangular flaps, to create a reconstructed nipple-areolar complex.

10. The method of claim 9 wherein the dissecting step comprises dissecting rectangular flaps wider distally than their respective widths at their proximal connections.

11. The method of claim 9 wherein the dissecting step comprises dissecting rectangular flaps wider proximally and distally than their respective widths at intervening locations on each flap.

12. The method of claim 9 wherein the dissecting step comprises including subcutaneous tissue beneath the nipple flap or one of the rectangular flaps, thereby providing increased volume to the reconstructed nipple-areolar complex.

13. The method of claim 12 wherein the dissecting step comprises including adipose, muscle, and/or scar tissue beneath the nipple flap or one of the rectangular flaps.

14. The method of claim 12 further comprising a step of circumscribing a perimeter of the reconstructed nipple-areolar complex with a substantially circular template, to facilitate obtaining a substantially circular shape for the reconstructed complex.

15. The method of claim 14 further comprising a step of incising along the perimeter, and undermining breast skin adjacent to the perimeter of the nipple-areolar complex; and, closing the perimeter incision with purse string suturing.

16. The method of claim 12 further comprising a step of deepithelializing a cutaneous area corresponding to the area of an areola; and, grafting cutaneous tissue to the deepithelialized area; or, tattooing an area corresponding to the area of an areola.

17. The method of claim 1 further comprising removing the expander after the expanding step.

18. The method of claim 17 further comprising removing the expander through an expander incision on the breast.

19. The method of claim 18 further comprising placing a permanent implant through the expander incision on the breast.

20. A method for reconstructing a breast comprising a nipple from an expanded breast envelope, said method comprising steps of:

performing a mastectomy which substantially preserves a cutaneous breast envelope;

placing a breast expander beneath a muscle;

expanding the cutaneous envelope, whereby the expanded envelope is at least as large as a contralateral breast;

providing a time period sufficient for growth of neovascular connections between the muscle and at least a portion of the envelope; and, reconstructing a nipple with the expanded neovascularized portion of the envelope, whereby the expanding step directly contributed an amount of tissue that permitted achievement of the breast reconstruction.

21. The method of claim 20 wherein the expander placing step occurs during a surgical procedure that also comprises the mastectomy step, or occurs as a separate surgical procedure from the mastectomy step.

22. The method of claim 20 wherein the expander placing step comprises placing an expander that requires approval pursuant to the Federal Food Drug, and Cosmetic Act; the Public Health Service Act; or, the Clinical Laboratories Improvement Act.

23. The method of claim 20 wherein the expander placing step comprises placing an expander comprising a means for segmental expansion; and, the nipple reconstruction step comprises reconstruction with neovascularized tissue that was expanded by a segment of the segmental expander.

24. The method of claim 20 wherein the expander placing step comprises placing an expander beneath a pectoralis, serratus anterior, latissimus dorsi or rectus abdominous muscle.

25. The method of claim 20 wherein the expanding step and the step of providing time for neovascularization are contemporaneous.

26. The method of claim 20 wherein the nipple reconstructing step further comprises reconstructing an areola.

27. The method of claim 26 wherein the nipple reconstructing step comprises performing a bowtie technique for nipple-areolar reconstruction.

28. The method of claim 20 further comprising removing the expander after the expanding step.

29. The method of claim 28 further comprising removing the expander through an expander incision on the breast.

30. The method of claim 29 further comprising a step of placing a permanent breast implant through the expander incision on the breast.

31. The method of claim 30 wherein the implant placing step comprises placing an implant that requires approval pursuant to the Federal Food Drug, and Cosmetic Act; the Public Health Service Act; or, the Clinical Laboratories Improvement Act.

32. The method of claim 30 wherein the implant placing step is the same step as the expander placing step, and wherein the expander is also a permanent implant.

* * * * *